(12) United States Patent
Modayur

(10) Patent No.: US 12,272,054 B2
(45) Date of Patent: Apr. 8, 2025

(54) SYSTEMS AND METHODS FOR DEVELOPMENTAL MONITORING OF CHILDREN

(71) Applicant: BSOLUTIONS, INC., Seattle, WA (US)

(72) Inventor: Bharath Modayur, Seattle, WA (US)

(73) Assignee: BSOLUTIONS, INC., Seattle, WA (US)

(*) Notice: Subject to any disclaimer, the term of this patent is extended or adjusted under 35 U.S.C. 154(b) by 339 days.

(21) Appl. No.: 17/735,650

(22) Filed: May 3, 2022

(65) Prior Publication Data
US 2022/0358645 A1 Nov. 10, 2022

Related U.S. Application Data

(60) Provisional application No. 63/183,785, filed on May 4, 2021.

(51) Int. Cl.
*G06T 7/00* (2017.01)
*G16H 15/00* (2018.01)
*G16H 40/67* (2018.01)

(52) U.S. Cl.
CPC .......... *G06T 7/0012* (2013.01); *G16H 15/00* (2018.01); *G16H 40/67* (2018.01); *G06T 2207/30004* (2013.01)

(58) Field of Classification Search
CPC ......... G06T 7/0012; G06T 2207/30004; G06T 7/0016; G06T 7/68; G06T 2207/10016; G06T 2207/20084; G06T 2207/30196; G06T 2207/30201; G16H 15/00; G16H 40/67; G16H 30/40; G16H 50/20; G16H 50/30
See application file for complete search history.

(56) References Cited

U.S. PATENT DOCUMENTS

| | | | | |
|---|---|---|---|---|
| 10,702,150 | B2* | 7/2020 | Klin | A61B 5/168 |
| 11,813,054 | B1* | 11/2023 | Dawson | G06T 7/246 |
| 2021/0133509 | A1* | 5/2021 | Wall | A61B 5/4088 |
| 2021/0236026 | A1* | 8/2021 | Davis | G06T 7/0012 |
| 2021/0267492 | A1* | 9/2021 | Fry | A61B 5/6829 |
| 2021/0275089 | A1* | 9/2021 | Long | A61B 5/4809 |

(Continued)

OTHER PUBLICATIONS

"MIMM Remote Parent Guidance 3 months boonzaaijer," Hogeschool utrecht university of applied science, 2013, pp. 2.

(Continued)

*Primary Examiner* — Dhaval V Patel
(74) *Attorney, Agent, or Firm* — WORKMAN NYDEGGER

(57) ABSTRACT

A system for facilitating developmental monitoring of children comprises one or more processors and one or more hardware storage devices storing instructions that are executable by the one or more processors to configure the system to (i) access a set of image data depicting a subject, (ii) extract a set of features from the set of image data, the set of features indicating one or more body characteristics of the subject as represented in the set of image data, and (iii) determine a set of developmental metrics for the subject based upon the set of features, the set of developmental metrics being indicative of a developmental state for the subject.

20 Claims, 9 Drawing Sheets

(56) References Cited

U.S. PATENT DOCUMENTS

2022/0101984 A1* 3/2022 Park .................. G06V 10/70
2022/0142535 A1* 5/2022 Burstein ............... A61B 5/441

OTHER PUBLICATIONS

"MIMM Remote Parent Guidance 6 months boonzaaijer," Hogeschool utrecht university of applied science, 2013, pp. 2.
Adams. A. et al., "NICU Parent Educational Empowerment Program," AOTA, 2022, pp. 7.
Adolph. K.E. et al., "Learning to Crawl," Child Development, vol. 69, No. 5, 1998, pp. 1299-1312.
Aimsamrarn. P. et al., "Cultural translation and adaptation of the Alberta Infant Motor Scale Thai version," Early Human Development, vol. 130, 2019, pp. 65-70.
Ali. J. B. et al., "Early Motor Differences in Infants at Elevated Likelihood of Autism Spectrum Disorder and/or Attention Deficit Hyperactivity Disorder," Journal of Autism and Developmental Disorders, vol. 50, 2020, pp. 4367-4384.
Atkins. K.L. et al., "Early Intervention Referral Outcomes for Children at Increased Risk of Experiencing Developmental Delays," Maternal and Child Health Journal, vol. 24, 2020, pp. 204-212.
Bai. D.L. et al., "Locomotor Status and the Development of Spatial Search Skills," Child Development, vol. 63, 1992, pp. 215-226.
Bartlett. D. et al., "Mothers' Difficulty in Assessing the Motor Development of Their Infants Born Preterm: Implications for Intervention," Infants Born Preterm, 1994, pp. 55-59.
Bertenthal. B.I. et al., "A Reexamination of Fear and Its Determinants on the Visual Cliff," Psychophysiology, vol. 21, No. 4, 1984, pp. 413-417.
Bertenthal. B.I. et al., "An Epigenetic Perspective on the Development of Self-Produced Locomotion and Its Consequences," Current Directions in Psychological Science, vol. 3, No. 5, 1994, pp. 140-145.
Bodnarchuk. J.L. et al., "Can parent reports be trusted? Validity of daily checklists of gross motor milestone attainment," Applied Developmental Psychology, vol. 25, 2004, pp. 481-490.
Boonzaaijer. M. et al., "A home-video method to assess infant gross motor development: parent perspectives on feasibility," BMC Pediatrics, vol. 19, Issue 392, 2019, pp. 12.
Boonzaaijer. M. et al., "Concurrent Validity Between Live and Home Video Observations Using the Alberta Infant Motor Scale," Pediatric Physical Therapy, 2017, pp. 146-151.
Brouwer. S.I. et al., "Later achievement of infant motor milestones is related to lower levels of physical activity during childhood: the GECKO Drenthe cohort," BMC Pediatrics, vol. 19, Issue 388, 2019, pp. 8.
Brown. C. et al., "The effect of mHealth and conventional awareness campaigns on caregivers' developmental literacy," Early Child Development and Care, 2020, pp. 13.
Campbell. J.M. et al., "Knowledge of Autism for Parents of Low Income with Low Literacy: Description and Relationship to Child Development Knowledge," Advances in Neurodevelopmental Disorders, vol. 3, 2019, pp. 8-16.
Campos. J.J. et al., "Early Experience and Emotional Development: The Emergence of Wariness of Heights," Psychological Science, vol. 3, No. 1, 1992, pp. 61-64.
Carballo-Fazanes. A. et al., "Intra-Rater (Live vs. Video Assessment) and Inter-Rater (Expert vs. Novice) Reliability of the Test of Gross Motor Development—Third Edition," Int. J. Environ. Res. Public Health, vol. 18, 2021, pp. 12.
Case-Smith. J. et al., "Systematic Review of Interventions Used in Occupational Therapy to Promote Motor Performance for Children Ages Birth—5 Years," American Journal of Occupational Therapy, vol. 67, 2013, pp. 413-424.
Chambers. C. et al., "Computer Vision to Automatically Assess Infant Neuromotor Risk," IEEE Transactions on Neural Systems and Rehabilitation Engineering, vol. 28, No. 11, Nov. 2020, pp. 2431-2442.
Chawarska. K. et al., "Parental Recognition of Developmental Problems in Toddlers with Autism Spectrum Disorders," J Autism Dev Disord, vol. 37, 2007, pp. 62-72.
Chi. L. D. et al., "An explanatory model of factors related to well baby visits by age three years for Medicaid-enrolled infants: a retrospective cohort study," BMC Pediatrics, vol. 13, Issue 158, 2013, pp. 9.
Darrah. et al., "Have infant gross monitor abilities changed in 20 years? A re-evaluation of Alberta Infant Motor Scale normative values," Developmental Medicine & Child Neurology, vol. 56, Mar. 29, 2014, pp. 877-881.
Darrah. J. et al., "Assessment of gross motor skills of at-risk infants: predictive validity of the Alberta Infant Motor Scale," Developmental Medicine & Child Neurology, vol. 40, 1998, pp. 485-491.
Darrah. J. et al., "Stability of serial assessments of motor and communication abilities in typically developing infants—implications for screening," Early Human Development, vol. 72, 2003, pp. 97-110.
DeGuzman. P.B. et al., "Rural disparities in early childhood well child visit attendance," Journal of Pediatric Nursing, vol. 58, 2021, pp. 76-81.
Dudek-Shriber. L. et al., "The Effects of Prone Positioning on the Quality and Acquisition of Developmental Milestones in Four-Month-Old Infants," Pediatric Physical Therapy, 2007, vol. 19, 2007, pp. 48-55.
Dumas. H.M. et al., "Pediatric Evaluation of Disability Inventory Computer Adaptive Test (PEDI-CAT) and Alberta Infant Motor Scale (AIMS): Validity and Responsiveness," Physical Therapy, vol. 95, No. 11, 2015, pp. 1559-1568.
Duncan. K. et al., "Parent handling of typical infants varies segmentally across development of postural control," Experimental Brain Research, vol. 236, 2018, pp. 645-654.
Einspieler. C. et al., "Early markers for cerebral palsy: insights from the assessment of general movements," Future Neurology, vol. 7, Issue 6, 2012, pp. 8.
Esposito. G. et al., "An exploration of symmetry in early autism spectrum disorders: Analysis of lying," Brain & Development, vol. 31, 2009, pp. 131-138.
Esposito. G. et al., "Symmetry in Infancy: Analysis of Motor Development in Autism Spectrum Disorders," Symmetry, vol. 1, 2009, pp. 215-225.
Estes. A. et al., "Behavioral, cognitive, and adaptive development in infants with autism spectrum disorder in the first 2 years of life," Journal of Neurodevelopmental Disorders, vol. 7, Issue 24, 2015, pp. 10.
Fenick. A.M. et al., "A Randomized Controlled Trial of Group Well-Child Care: Improved Attendance and Vaccination Timeliness," Clinical Pediatrics, vol. 59, Issue 7, 2020, pp. 686-691.
Flanagan. J.E. et al., "Head Lag in Infants at Risk for Autism: A Preliminary Study," American Journal of Occupational Therapy, vol. 66, 2012, pp. 577-585.
Fuentefria. R. et al., "Motor development of preterm infants assessed by the Alberta Infant Motor Scale: systematic review article," J Pediatr (Rio J)., vol. 93, Issue 4, 2017, pp. 328-342.
Fulceri. F. et al., "Early motor abnormalities in autism spectrum disorders: evidence from preclinical and clinical research," Int. J. Sport Psychol, vol. 48, 2017, pp. 555-568.
Gabis. L.V. et al., "Motor delay—An early and more common "red flag" in girls rather than boys with autism spectrum disorder," Research in Developmental Disabilities, vol. 104, 2020, 103702, pp. 9.
Gontijo. A.P. et al., "Commentary on Cross-Cultural Validity: Canadian Norm Values of the Alberta Infant Motor Scale Evaluated for Dutch Infants," Cross-Cultural Validity, 2019, p. 359.
Guidetti. J. et al., "The Effect of Positional Support on Tolerance of Wakeful Prone in Infants," Physical & Occupational Therapy in Pediatrics, vol. 37, Issue 3, 2017, pp. 308-321.
Guzman. L. et al., "First-Time Parents' Knowledge of Early Child Development," Focus Group Report, 2018, pp. 35.
Haque. M.M. et al., "Informing Developmental Milestone Achievement for Children With Autism: Machine Learning Approach," JMIR Med Inform, vol. 9, Issue 6, 2021, e29242, pp. 21.

(56) References Cited

OTHER PUBLICATIONS

Harrison. M. et al., "General Pediatrician-Staffed Behavioral/Developmental Access Clinic Decreases Time to Evaluation of Early Childhood Developmental Disorders," Journal of developmental and behavioral pediatrics, vol. 38, Issue 6, 2017, pp. 353-357.
Hendrix. R.R. et al., "Development of Self-Produced Locomotion in the First Year: Changes in Parent Perceptions and Infant Behaviour," Infant and Child Development, 2010, pp. 13.
Higgins. C.I. et al., "Effect of Self-Produced Locomotion on Infant Postural Compensation to Optic Flow," Developmental Psychology, vol. 32, No. 5, 1996, pp. 836-841.
Huges. A.J. et al., "Motor Development Interventions for Preterm Infants: A Systematic Review and Meta-analysis," Pediatrics, vol. 138, No. 4 , Oct. 2016, pp. 15.
Irshad. M.T. et al., "AI Approaches towards Prechtl's Assessment of General Movements: A Systematic Literature Review," Sensors, vol. 20, 2020, 5321, pp. 32.
Iverson. J.M. et al., "Early Motor Abilities in Infants at Heightened Versus Low Risk for ASD: A Baby Siblings Research Consortium (BSRC) Study," American Psychological Association, vol. 128, No. 1, 2019, pp. 69-80.
Jimenez. M.E. et al., "A Pilot Randomized Trial of a Video Patient Decision Aid to Facilitate Early Intervention Referrals From Primary Care," Clinical Pediatrics, vol. 56, Issue 3, 2017, pp. 268-277.
Jimenez. M.E. et al., "The Impact of Parental Health Literacy on the Early Intervention Referral Process," Journal of Health Care for the Poor and Underserved, vol. 24, No. 3, 2013, pp. 1053-1062.
Kawashima. K. et al., "Video-based evaluation of infant crawling toward quantitative assessment of motor development," Scientific Reports, vol. 10, 2020, pp. 12.
Kirthika. V. et al., "Reliability of Alberta Infant Motor Scale Using Recorded Video Observations Among the Preterm Infants in India: A Reliability Study," Journal of Health and Allied Sciences, vol. 16, Issue 3, 2017, pp. 4.
Ko. J. et al., "Reliability Study of the Items of the Alberta Infant Motor Scale (AIMS) Using Kappa Analysis," Int. J. Environ. Res. Public Health, vol. 19, Issue 1767, 2022, pp. 10.
Kolobe. T. et al., "Comparison of two outcome measures for infants with cerebral palsy and infants with motor delays," Physical Therapy, vol. 78, Issue 10, 1998, pp. 9.
Landa. R. J., "Efficacy of early interventions for infants and young children with, and at risk for, autism spectrum disorders," Int Rev Psychiatry., vol. 30, Issue 1, 2018, pp. 25-39.
Leckey. Y. et al., "Parent and facilitator experiences of an intensive parent and infant programme delivered in routine community settings," Primary Health Care Research & Development, vol. 20, 2019, pp. 12.
Liao. P-J.M. et al., "Examination of the Item Structure of the Alberta Infant Motor Scale," Pediatric Physical Therapy, 2004, pp. 31-38.
Lurio. J.G. et al., "Recognition and Management of Motor Delay and Muscle Weakness in Children," American Family Physician, vol. 91, No. 1, 2015, pp. 38-44.
Luu. T.M. et al., "Web-Based Intervention to Teach Developmentally Supportive Care to Parents of Preterm Infants: Feasibility and Acceptability Study," JMIR Res Protoc, vol. 6, Issue 11, 2017, e236, pp. 11.
Mason. A.N. et al., "A Review of Alberta Infant Motor Scale (AIMS)," Physical and Rehabilitation Medicine, vol. 30, Issue 3, 2018, pp. 255-258.
May. T. et al., "A Multidisciplinary Perspective on Motor Impairment as an Early Behavioural Marker in Children with Autism Spectrum Disorder," Australian Psychologist, vol. 51, 2016, pp. 296-303.
Mazumdar. P. et al., "Early detection of children with Autism Spectrum Disorder based on visual exploration of images," Signal Processing: Image Communication, vol. 94, 2021, 116184, pp. 8.
McManus. B.M. et al., "Child characteristics and early intervention referral and receipt of services: a retrospective cohort study," BMC Pediatrics, vol. 20, Issue 84, 2020, pp. 10.
McManus. B.M. et al., "Predictors of receiving therapy among very low birth weight 2-year olds eligible for Part C early intervention in Wisconsin," BMC Pediatrics, vol. 13, Issue 106, 2013, pp. 9.
Mendelsohn. A.L. et al., "Assessing the Impacts of Pediatric Primary Care Parenting Interventions on EI Referrals Through Linkage With a Public Health Database," Journal of Early Intervention, vol. 42, Issue 1, 2020, pp. 69-84.
Morgan. C. et al., "Optimising motor learning in infants at high risk of cerebral palsy: a pilot study," BMC Pediatrics, vol. 15, Issue 30, 2015, pp. 11.
Nguyen-Thai. B. et al., "A Spatio-temporal Attention-based Model for Infant Movement Assessment from Videos," IEEE Journal of Biomedical and Health Informatics, vol. 25, Issue 10, 2021, pp. 10.
Novak. I. et al., "Early, Accurate Diagnosis and Early Intervention in Cerebral Palsy Advances in Diagnosis and Treatment," JAMA Pediatr, vol. 171, Issue 9, 2017, pp. 897-907.
Oberg. G.K. et al., "Study protocol: an early intervention program to improve motor outcome in preterm infants: a randomized controlled trial and a qualitative study of physiotherapy performance and parental experiences," BMC Pediatrics, vol. 12, Issue 15, 2012, pp. 9.
Pineda. R.G. et al., "Head Lag in Infancy: What Is It Telling US?," American Journal of Occupational Therapy, vol. 70, 2016, pp. 8.
Plamer. C.F. et al., "Moving into tummy time, together: Touch and transitions aid parent confidence and infant development," Infant Ment Health J., vol. 40, 2019, pp. 277-288.
Poggoilo. M. et al., "Effects of a Home-Based Family-Centred Early Habilitation Program on Neurobehavioural Outcomes of Very Preterm Born Infants: A Retrospective Cohort Study," Neural Plasticity, 2016, pp. 10.
Rikhy. S. et al., "Gauging knowledge of developmental milestones among Albertan adults: a cross-sectional survey," BMC Public Health, vol. 10, Issue 183, 2010, pp. 9.
Salazar. B.L., "Supporting the Paternal Role and Transition Home From the NICU: A Mixed Method Study," The Open Journal of Occupational Therapy, vol. 10, Issue 2, 2022, pp. 21.
Sand. N. et al., "Pediatricians' Reported Practices Regarding Developmental Screening: Do Guidelines Work? Do They Help?," Pediatrics, vol. 116, No. 1, 2015, pp. 174-179.
Schroeder. A.S. et al., "General Movement Assessment from videos of computed 3D infant body models is equally effective compared to conventional RGB video rating," Early Human Development, vol. 144, 2020, 104967, pp. 8.
Serdarevic. F. et al., "Infant Muscle Tone and Childhood Autistic Traits A Longitudinal Study in the General Population," Autism research, vol. 10, Issue 5, 2017, pp. 757-768.
Sgandurra. G. et al., "A pilot study on early home-based intervention through an intelligent baby gym (CareToy) in preterm infants," Research in Developmental Disabilities, vol. 53-54, 2016, pp. 32-42.
Singh. P. et al., "The importance of early identification and intervention for children with developmental delays," Indian journal of positive psychology, vol. 9, Issue 2, 2018, pp. 233-237.
Stankevich. Y. et al., "Psychometric Properties of an Abbreviated Version of the Apathy Evaluation Scale for Parkinson Disease (AES-12PD)," The American journal of geriatric psychiatry, vol. 26, Issue 10, 2018, pp. 1079-1090.
Steyerberg. E.W. et al., "Risk prediction with machine learning and regression methods," Biometrical Journal, vol. 56, Issue 4, 2014, pp. 601-606.
Suir. I. et al., "Cross-Cultural Validity: Canadian Norm Values of the Alberta Infant Motor Scale Evaluated for Dutch Infants," Pediatric Physical Therapy, 2019, pp. 354-358.
Suir. I. et al., "The AIMS home-video method: parental experiences and appraisal for use in neonatal follow-up clinics," BMC Pediatrics, vol. 22, Issue 338, 2022, pp. 11.
Syrengelas. D. et al., "Alberta Infant Motor Scale (AIMS) Performance of Greek Preterm Infants: Comparisons With Full-Term Infants of the Same Nationality and Impact of Prematurity-Related Morbidity Factors," Physical Therapy, vol. 96, No. 7, 2016, pp. 1102-1108.

(56) References Cited

OTHER PUBLICATIONS

Taanila. A. et al., "Infant developmental milestones: a 31-year follow-up," Developmental Medicine & Child Neurology, vol. 47, 2005, pp. 581-586.

Talbott. M.R. et al., "Brief Report: Preliminary Feasibility of the TEDI: A Novel Parent-Administered Telehealth Assessment for Autism Spectrum Disorder Symptoms in the First Year of Life," Journal of Autism and Developmental Disorders, vol. 50, 2020, pp. 3432-3439.

Thomas. R.E. et al., "Rates of detection of developmental problems at the 18-month well-baby visit by family physicians' using four evidence-based screening tools compared to usual care: a randomized controlled trial," Child: care, health and development, vol. 42, Issue 3, 2016, pp. 382-393.

Valvano. J. et al., "Activity-focused Motor Interventions for Infants and Young Children With Neurological Conditions," Infants & Young Children, vol. 19, No. 4, 2006, pp. 292-307.

West. K. L., "Infant Motor Development in Autism Spectrum Disorder: A Synthesis and Meta-analysis," Child Development, vol. 90, No. 6, 2019, pp. 2053-2070.

Wu. Y-C. et al., "A randomized controlled trial of clinic-based and home-based interventions in comparison with usual care for preterm infants: Effects and mediators," Research in Developmental Disabilities, vol. 35, 2014, pp. 2384-2393.

Zachry. A.H. et al., "Caregiver Awareness of Prone Play Recommendations," The American Journal of Occupational Therapy, vol. 65, No. 1, 2011, pp. 101-105.

Zoghi. A. et al., "The Impact of Home Motor Affordances on Motor, Cognitive and Social Development of Young Children," Iran J Child Neurol. Spring, vol. 13, Issue 2, 2019, pp. 61-69.

Zwaigenbaum. L. et al., "Early identification of autism spectrum disorders," Behavioural Brain Research, vol. 251, 2013, pp. 133-146.

* cited by examiner

Activities
Early Markers

Today

Encourage bringing hands to feet

Both Ella's left & right sides are engaged

Progress
Early Markers

Amy's Motor Development
From over 6 hours of data

SYSTEMS AND METHODS FOR DEVELOPMENTAL MONITORING OF CHILDREN

CROSS-REFERENCE TO RELATED APPLICATIONS

This application claims priority to U.S. Provisional Patent Application No. 63/183,785, filed May 4, 2021 and entitled "A home-based screening and intervention tool for developmental monitoring of infants and toddlers", the entirety of which is incorporated herein by reference.

STATEMENT REGARDING GOVERNMENT-SPONSORED RESEARCH

The invention was made with government support under Small Business Innovation Research (SBIR) grant HD095783 awarded by The National Institutes of Health. The government may have certain rights in the invention.

BACKGROUND

Most child development unfolds at home and is not visible to clinicians. Not all parents are able to attend well-child visits, and even when they do, comprehensive screening is not possible due to resource limitations and time restrictions associated with such visits. Clinicians often rely on parent-based reports to determine how a child is developing. However, the accuracy and/or usefulness of parent-based reports is/are reliant on the parent's skill in observing and eliciting behaviors from the child. Parent-based reports are further subject to parents' ability to recall relevant information to provide to clinicians.

During clinical visits, clinicians are usually unable to perform comprehensive screenings for assessing child development in view of the time and/or resource constraints associated therewith. Even when children are in a clinical situation for prolonged periods (e.g., a neonatal intensive care unit (NICU)), experts with specific expertise that can evaluate child developmental markers and/or assess risks are not always present or available. Experts may thus fail to observe important indicators of developmental progression.

The foregoing constraints can cause parents, clinicians, and/or caregivers to fail to properly detect developmental conditions and/or concerns in children, even when the child exhibited behaviors indicative of such developmental conditions and/or concerns.

Accordingly, there is a need for improved systems, methods, and/or techniques for facilitating developmental monitoring of children (e.g., infants and toddlers), such as to enable early flagging of risks so that appropriate interventional support can be initiated to improve health outcomes.

The subject matter described herein is not limited to embodiments that solve any disadvantages or that operate only in environments such as those described above. Rather, this background is only provided to illustrate one exemplary technology area where some embodiments described herein may be practiced.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which.

DETAILED DESCRIPTION

Figure 1:
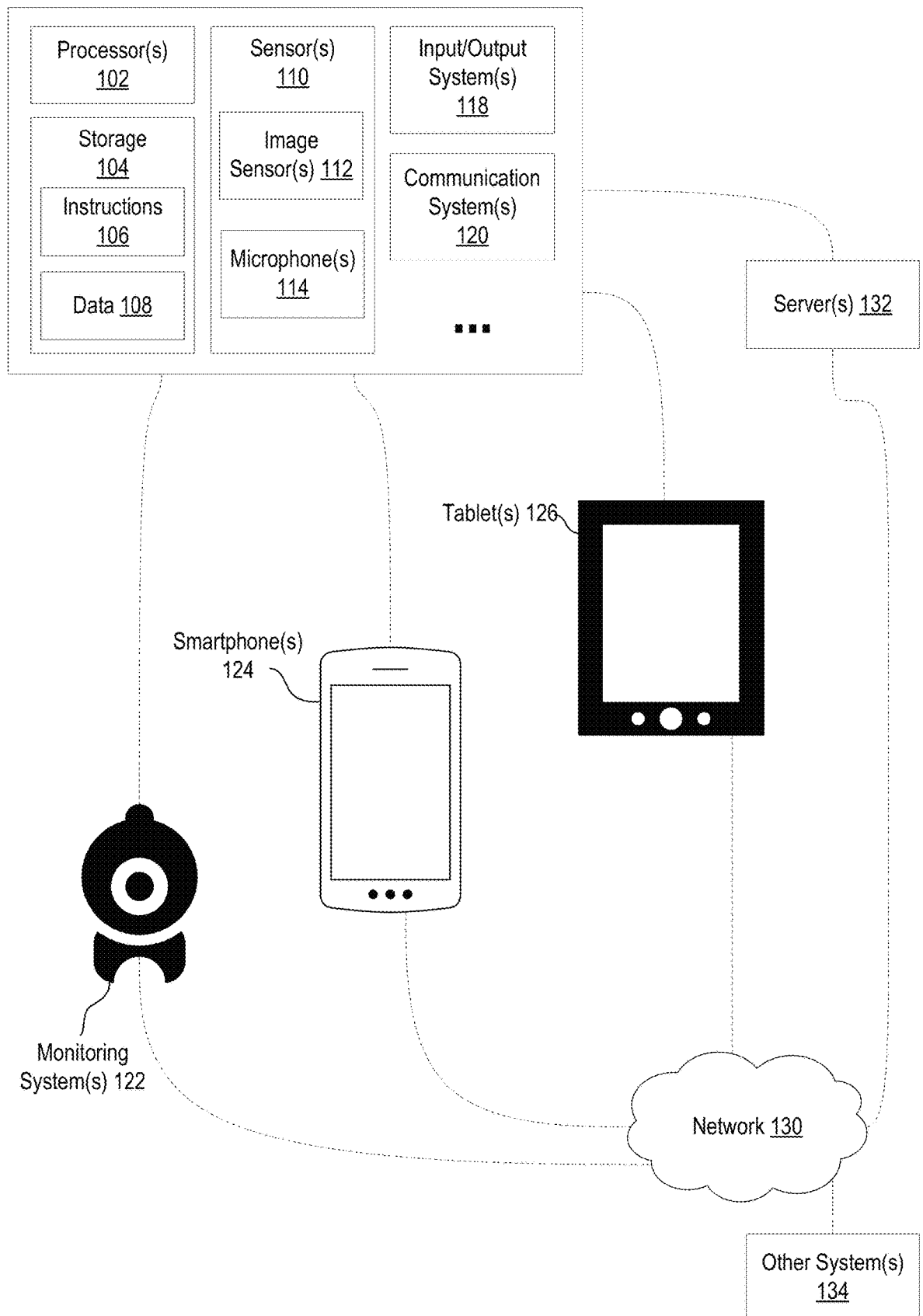
FIG. 1 illustrates example components of example systems that may comprise or implement the disclosed embodiments.

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the particular example terminology used herein is for the purpose of describing the embodiments and is not necessarily intended to limit the scope of the claimed invention.

As noted above, conventional approaches for assessing child development are limited by the adeptness of parents in observing and/or eliciting child behavior and accurately/completely reporting such behavior to clinicians during infrequent clinical visits. Even where children are in long-term clinical situations, clinicians are not constantly present and are therefore unable to directly monitor all child behavior. Child developmental conditions and/or concerns can therefore easily go undetected, leading to improper and/or sub-optimal care decisions for the affected children.

The present disclosure is directed to improved systems, methods, and techniques for facilitating developmental monitoring of children (e.g., infants, toddlers, etc.). Disclosed embodiments may enable meaningful observation and/or developmental analysis of children over longer periods than conventional approaches (e.g., relative to short clinical encounters). Such observation may advantageously be performed in various settings and/or without the direct physical presence of skilled clinicians (e.g., while the child is being cared for within a residence).

Disclosed embodiments involve capturing and/or accessing image data depicting a subject (e.g., a child) and extracting a set of features from the image data, which may indicate body characteristics of the subject such as body joint positions and/or facial landmarks. The image data may advantageously be captured in the absence of skilled clinicians (or within clinical settings) using devices that are readily accessible to caregivers (e.g., baby monitoring devices, smartphones, security cameras, tablets, and/or others). The image data may be part of a video stream captured over a time period, such that the extracted features depict (changes in) body joint positions and/or facial landmarks over the time period. The set of features may be based upon image data captured during different imaging/recording sessions. As such, features may be obtained representing the subject at different time periods, in different locations, and/or during different states and/or activities of the subject.

Developmental metrics are determined using the set of features. As will be described in more detail hereinafter, developmental metrics may include, by way of example, body symmetry, head symmetry, motion attributes, motor scores, milestone achievement, and/or others. The developmental metrics may be used to track the developmental progress of the subject. For example, the developmental metrics may be presented to skilled clinicians (or other caregivers), enabling the clinicians to draw inferences about the developmental progress of the subject (even where at least some of the image data upon which the developmental metrics are based are captured outside of the presence of the clinicians).

In some instances, a developmental state is determined based upon the developmental metrics (e.g., indicating developmental conditions for the subject, such as whether the subject appears to be experiencing cognitive, sensory, motor, or other developmental delays). The developmental state may be presented to caregivers to influence the care decisions undertaken by the caregivers for the subject. In some instances, interventional activities are determined based upon the developmental state, which may be presented to caregivers to allow the caregivers to take action for improving the developmental state of the subject.

In some instances, additional or alternative information is used for determining developmental metrics for a subject, such as voice characteristics of the subject and/or input provided by a caretaker of the subject. For example, a user device associated with a caregiver may prompt the caregiver to provide input indicating certain information for the subject (e.g., by prompting the caregiver to provide voice, text, or other input), which can be used as additional context and/or to supplement the information derived from the image data for determining the developmental metrics.

The disclosed embodiments may allow parents and/or caregivers to receive developmental metrics for their children. For example, data captured in accordance with the present disclosure may indicate that a child is not spending sufficient time on the child's belly (according to the child's age). Disclosed systems may cause a notification to be presented to parents and/or caregivers pointing out the need to increase the amount of time the child spends on the child's belly. Such notification may additionally or alternatively provide a plan for carrying out the needed intervention.

Implementing the disclosed embodiments may provide an asynchronous telehealth solution for tracking, monitoring, and/or intervening in child development. For example, developmental metrics obtained by implementing the disclosed embodiments may be reviewed retrospectively by clinicians, eliminating the need for clinicians to be physically present to directly observe important child behaviors/characteristics and eliminating the need for parents to recognize and/or recall exhibitions of such behaviors/characteristics.

Implementing the disclosed embodiments may enable targeted interventional activities to be planned for specific children. Such activities may be provided to parents and/or caregivers for performance with the child(ren). These activities can promote development of the infant in domains such as sensory, motor, cognitive, etc. Additionally, disclosed embodiments can enable continued tracking to observe the effectiveness of implementing such interventional activities (e.g., developmental metrics may be tracked during the performance of the interventional activities).

Having just described some various high-level features and benefits of the disclosed embodiments, attention will now be directed to FIGS. 1 through 9. These Figures illustrate various conceptual representations, components, architectures, methods, and supporting illustrations related to the disclosed embodiments.

Example Systems and Techniques for Developmental Monitoring of Infants and Toddlers FIG. 1 illustrates example components of example systems that may comprise or implement the disclosed embodiments. For example, the components illustrated in FIG. 1 include processor(s) 102, storage 104, sensor(s) 110, input/output system(s) 118 (I/O system(s) 118), and communication system(s) 120. Although FIG. 1 illustrates particular components, one will appreciate, in view of the present disclosure, that systems for implementing the disclosed embodiments may comprise any number of additional or alternative components (as indicated by the ellipsis).

The processor(s) 102 may comprise one or more sets of electronic circuitries that include any number of logic units, registers, and/or control units to facilitate the execution of computer-interpretable instructions (e.g., instructions that form a computer program). Such computer-interpretable instructions may be stored within storage 104. The storage 104 may comprise physical system memory and may be volatile, non-volatile, or some combination thereof. Furthermore, storage 104 may comprise local storage, remote storage (e.g., accessible via communication system(s) 120 or otherwise), or some combination thereof. Additional details related to processors (e.g., processor(s) 102) and computer storage media (e.g., storage 104) will be provided hereinafter.

In some implementations, the processor(s) 102 may comprise or be configurable to execute any combination of software and/or hardware components that are operable to facilitate processing using machine learning models or other artificial intelligence-based structures/architectures. For example, processor(s) 102 may comprise and/or utilize hardware components or computer-executable instructions operable to carry out function blocks and/or processing layers configured in the form of, by way of non-limiting example, single-layer neural networks, feed forward neural networks, radial basis function networks, deep feed-forward networks, recurrent neural networks, long-short term memory (LSTM) networks, gated recurrent units, autoencoder neural networks, variational autoencoders, denoising autoencoders, sparse autoencoders, Markov chains, Hopfield neural networks, Boltzmann machine networks, restricted Boltzmann machine networks, deep belief networks, deep convolutional networks (or convolutional neural networks), deconvolutional neural networks, deep convolutional inverse graphics networks, generative adversarial networks, liquid state machines, extreme learning machines, echo state networks, deep residual networks, Kohonen networks, support vector machines, neural Turing machines, and/or others.

As will be described in more detail, the processor(s) 102 may be configured to execute instructions 106 stored within storage 104 to perform certain actions associated developmental monitoring of children. The actions may rely at least in part on data 108 stored on storage 104 in a volatile and/or non-volatile manner.

In some instances, the actions may rely at least in part on communication system(s) 120 for receiving data from remote system(s), which may include, for example, separate systems or devices, sensors, servers, cloud resources/services, and/or others. The communications system(s) 120 may comprise any combination of software or hardware components that are operable to facilitate communication between on-system components/devices and/or with off-system components/devices. For example, the communications system(s) 120 may comprise ports, buses, or other physical connection apparatuses for communicating with other devices/components. Additionally, or alternatively, the communications system(s) 120 may comprise systems/components operable to communicate wirelessly with external systems and/or devices through any suitable communication channel(s), such as, by way of non-limiting example, Bluetooth, ultra-wideband, WLAN (e.g., Wi-Fi), infrared communication, and/or others.

FIG. 1 illustrates that a system for implementing the disclosed embodiments may comprise or be in communication with I/O system(s) 118. I/O system(s) 118 may include any type of input or output device such as, by way of non-limiting example, a touch screen, a mouse, a keyboard, a controller, a speaker, and/or others, without limitation. For example, the I/O system(s) 118 may include a display system that may comprise any number of display panels, optics, laser scanning display assemblies, and/or other components.

Furthermore, FIG. 1 illustrates that a system for implementing the disclosed embodiments may comprise or be in communication with sensor(s) 110. Sensor(s) 110 may comprise any device for capturing or measuring data representative of perceivable or detectable phenomena. By way of non-limiting example, the sensor(s) 110 may comprise one or more image sensors (e.g., image sensor(s) 112), microphones (e.g., microphone(s) 114), thermometers, barometers, magnetometers, accelerometers, gyroscopes, and/or others. Image sensor(s) 112 may comprise charge-coupled device (CCD) image sensors, complementary metal-oxide-semiconductor (CMOS) image sensors, single photon avalanche diode (SPAD) image sensors, and/or any other type of image sensor configured to detect photons or electromagnetic radiation to capture imagery (e.g., intensity or grayscale images, RGB images, and/or others). In some instances, the sensor(s) 110 comprise one or more depth sensors, such as stereo cameras, time-of-flight cameras, rangefinders, and/or others.

The components shown in FIG. 1 may be implemented in various types and/or combinations of systems/devices. For example, any number of the components discussed hereinabove with reference to FIG. 1 may be implemented in association with monitoring system(s) 122 (e.g., baby monitors, security cameras, etc.), which may comprise sensor(s) 110 (e.g., image sensor(s) 112 and/or microphone(s) 114) configured to capture imagery and/or audio signals associated with a subject (e.g., a child). The monitoring system(s) 122 may comprise processor(s) 102 and/or storage 104 associated with operation of the sensor(s) 110 for capturing image and/or audio data representing the subject, and communication system(s) 120 configured for transmitting such data (or any information based thereon) to other devices/systems. Such functionality and/or components may additionally or alternatively be implemented on smartphone(s) 124, tablet(s) 126, and/or other system(s) 134 (e.g., specialized equipment for the clinical setting).

As indicated above, image and/or audio data (and/or any information based thereon) may be stored and/or transmitted among different devices. For example, FIG. 1 shows that the monitoring system(s) 122, the smartphone(s) 124, and the tablet(s) 126, and/or the other system(s) 134 may be in communication with a network 130. The network may comprise one or more links that enable the transport of information between and/or among systems, modules, and/or devices. FIG. 1 also illustrates server(s) 132 in communication with the monitoring system(s) 122, the smartphone(s) 124, and the tablet(s) 126, and/or the other system(s) 134 (directly or indirectly). The server(s) 132 may comprise any of the components discussed hereinabove with reference to FIG. 1, such as processor(s) 102, storage 104, I/O system(s) 118, communication system(s) 120, etc. The server(s) 132 may be configured to receive, process, and/or store information from the monitoring system(s) 122, the smartphone(s) 124, and the tablet(s) 126, and/or the other system(s) 134.

Various acts may be performed utilizing captured image data and/or audio to facilitate developmental monitoring of children. Such acts may be performed utilizing any suitable computing system(s) or device(s) operating singly or in combination (e.g., utilizing processor(s) 102, storage 104, and/or other components of monitoring system(s) 122, the smartphone(s) 124, and the tablet(s) 126, and/or the other system(s) 134).

Figure 2:
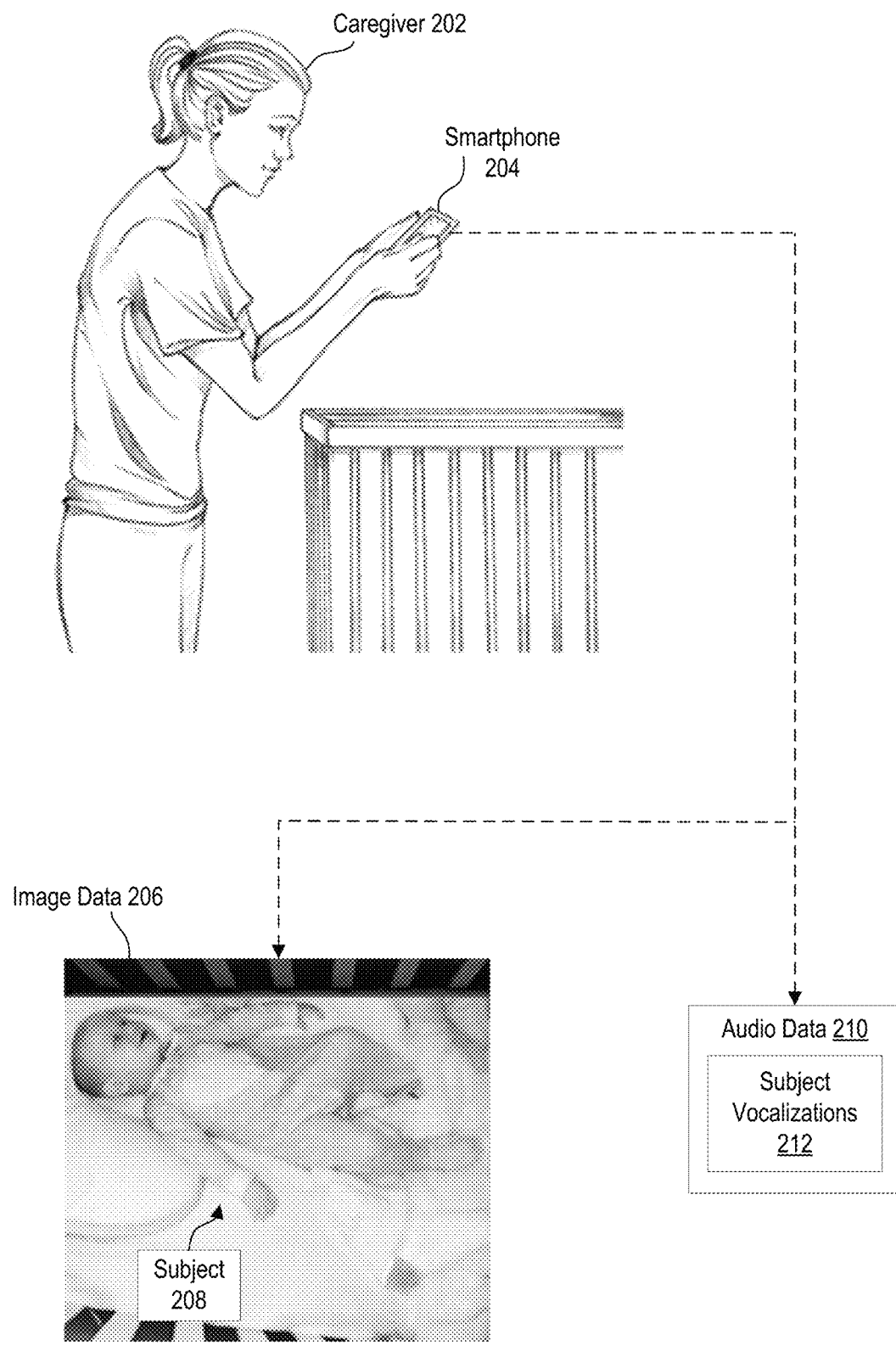
FIG. 2 illustrates an example conceptual representation of acquiring image data and audio data representative of a subject.

As noted above, various types of devices may be utilized to facilitate capturing of image and/or audio data depicting a subject (e.g., a child). FIG. 2 provides an example in which a caregiver 202 operates a smartphone 204 (e.g., corresponding in at least some respects to smartphone(s) 124 of FIG. 1) to capture image data 206 depicting a subject 208. In some instances, as shown in the example of FIG. 2, a device may additionally obtain audio data 210 which captures subject vocalizations 212.

The image data 206 may take on various forms, such as a set of one or more still images or video frames of a captured video (which may comprise accompanying audio). FIG. 2 depicts an example in which the caregiver 202 comprises an at-home caregiver (e.g., a parent, babysitter, relative, etc.) utilizing the smartphone 204 to capture the subject 208 while the subject is in a home setting (e.g., in the subject's sleeping area). One will appreciate, in view of the present disclosure, that the principles discussed are not limited to such situations. For instance, as used herein, a "caregiver" can comprise any entity with a relationship to the subject that conveys on the caregiver a responsibility to maintain or promote the wellbeing of the subject. In this regard, a caregiver may comprise a parent, guardian, family member (distant or immediate), person(s) with a professional relationship with the subject, such as a babysitter, nanny, daycare worker, teacher, steward, butler, medical practitioner (e.g., a nurse, pediatrician, physician, physician assistant, and/or others), and/or others.

Furthermore, as indicated above, although FIG. 2 illustrates a smartphone 204 utilized to capture the image data 206 and the audio data 210, other device configurations may be utilized in accordance with the present disclosure, such as a tablet, desktop computer, video camera, monitoring system (e.g., a baby monitor, security camera, etc.), and/or other system/device(s). It will be appreciated that different devices may be used to capture image data and audio data for the same subject.

In addition, although FIG. 2 shows the caregiver 202 as within the physical presence of the subject 208 during acquisition of the image data 206 and the audio data 210, image data 206 and/or audio data of the subject 208 may be captured in the absence of a caregiver 202. Still furthermore, image data 206 and/or audio data 210 may be captured in any suitable location(s) (e.g., at a caregiver's residence, at a public location such as a park, at a place of business such as a daycare center, at a medical care center such as a pediatrician's office, NICU, or other care setting, etc.).

The example of FIG. 2 illustrates the image data 206 capturing the subject 208 as the subject 208 is positioned within its sleeping area (e.g., a crib). The image data 206 may capture the subject 208 as the subject 208 engages in an unguided activity. An "unguided activity" comprises an activity in which a subject chooses actions to take without engaging with predefined instructions or structured steps provided by external sources (e.g., a caregiver or any person, an electronic device, written/printed instructions, etc.). An unguided activity does not include activities in which a subject perceives (or recalls), mentally processes, and pursues compliance with predefined instructions associated with predefined tasks or actions.

In this way, systems of the present disclosure may persistently acquire image data and/or audio data depicting the subject in natural situations. For example, a monitoring system may be positioned in an "always on" mode within a nursery, bedroom, play area, or other location within which the subject is frequently positioned and able to perform unguided activities.

In some instances, systems of the present disclosure may acquire image data (and/or audio data) capturing the subject as the subject responds to stimuli or states facilitated by external entities (e.g., a caretaker). For example, a system may capture image data and/or audio data as a caretaker calls out the subject's name, such that the image data and/or the audio data indicates an amount of time it takes for the subject to direct its gaze toward the caretaker after hearing its name. As another example, the system may capture image data and/or audio data of the caretaker placing an item within reach of the subject such that the image data and/or audio data captures the subject's body as the subject reaches for the item. Other diagnostic and/or interventional activities (which may be determined based upon captured image data and/or audio data as discussed hereinafter) may be represented in acquired image data and/or audio data.

Figure 3A:
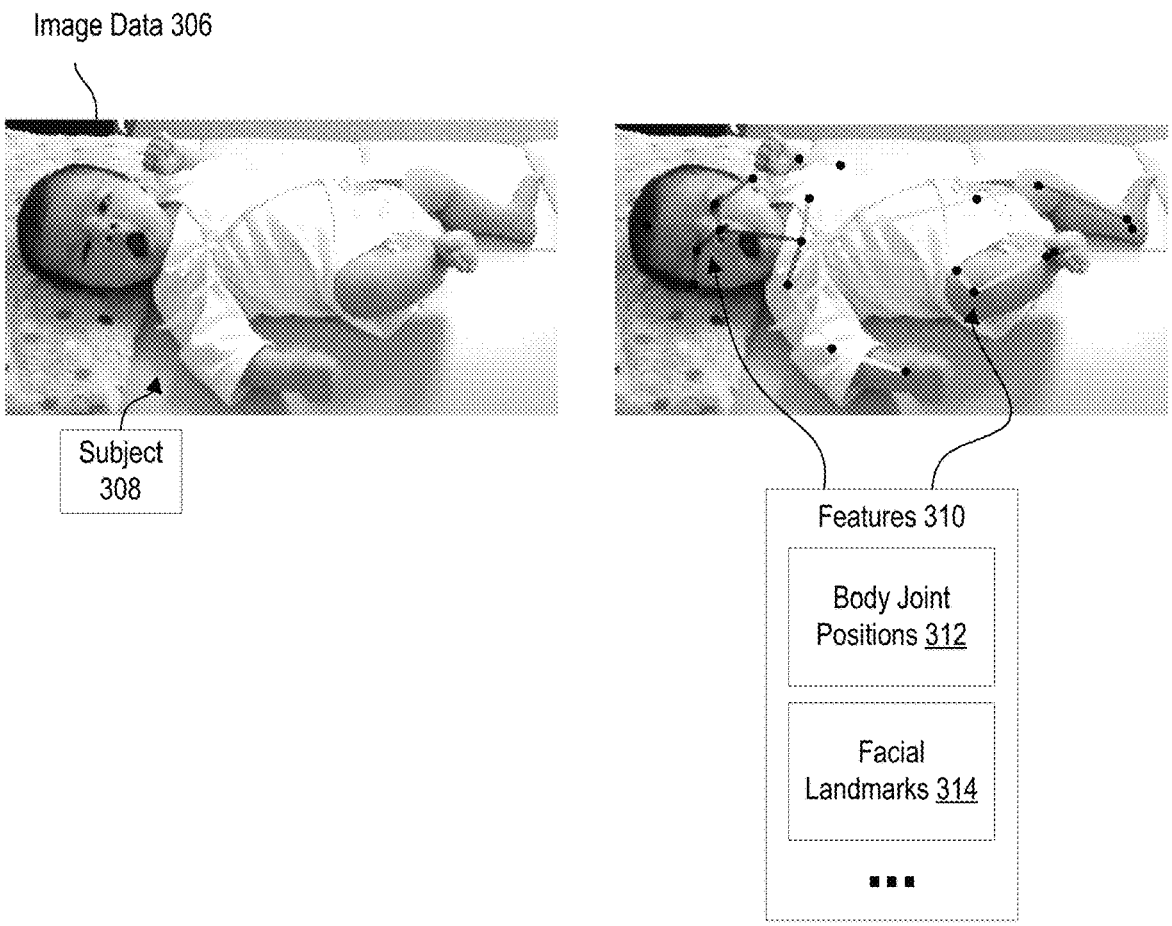
FIG. 3A illustrates a conceptual representation of determining features based upon image data of a subject.

FIG. 3A illustrates image data 306 depicting a subject 308 (similar to image data 206 capturing the subject 208. FIG. 3A conceptually depicts features 310 that may be extracted from the image data 306 of the subject 308. The features 310 indicate body characteristics of the subject 308 as captured in the image data 306. The example of FIG. 3A shows that such body characteristics may comprise body joint positions 312 and/or facial landmarks 314 (depicted in FIG. 3A by black dots with interconnecting lines). Other types of features may additionally or alternatively be extracted (indicated by the ellipsis).

The body joint positions 312 may be estimated utilizing any suitable technique, such as by utilizing texture descriptors (combining motion and appearance cues), motion energy features, spatial and/or temporal maps or relationships among recognized shapes, joint trajectory maps, joint distance maps, local accumulative frame features, artificial intelligence based approaches (e.g., utilizing DNN models, CNN models, RNN models), and/or others. In some instances, depth information (e.g., obtained via sensor(s) 110) is used in combination with image data 306 (e.g., RGB-D data) to determine the body joint positions 312 (and/or facial landmarks 314). The body joint locations/positions may indicate a quality of poses for the subject 308, such as asymmetry exhibited by the subject.

Facial landmarks 314 may be associated with key portions and/or nodal points of a human face, such as key portions of the eyes, nose, mouth, eyebrows, facial outline, forehead, and/or inter-eye distance, nose width, eye socket depth, distance from forehead to chin, and/or others. Any suitable facial feature recognition configuration may be utilized in accordance with the present disclosure, such as, by way of non-limiting example, MULTI-PIE, MUCT, XM2VTS, MENPO, AFLW, PUT, Caltech 10 k, BioID, HELEN, Face ID, and/or others.

As indicated above, the image data 306 may comprise still images or video frames, which may be captured at different timepoints (e.g., during different events and/or activities associated with the subject). In this regard, a set of image data used for determining features 310 may comprise multiple subsets of image data, each being associated with different timepoints or time periods. Accordingly, a set of features extracted from a set of image data may include multiple subsets of features, each being correspondingly associated with the different timepoints or time periods.

Figure 3B:
FIG. 3B illustrates a conceptual representation of determining voice characteristics based upon audio data capturing vocalizations of a subject.

FIG. 3B illustrates a conceptual representation of determining voice characteristics 330 based upon audio data 320 capturing subject vocalizations 322 (e.g., corresponding to the audio data 210 capturing subject vocalizations 212). Voice characteristics 330 may comprise pitch, length of sounds, loudness or prominence, timbre, and/or others, and may be extracted utilizing any suitable vocal feature extraction technique, such as Mel Frequency Cepstral Coefficients, Linear Prediction Coefficients, Linear Prediction Cepstral Coefficients, Line Spectral Frequencies, Discrete Wavelet Transform, Perceptual Linear Prediction, and/or others.

Figure 4:
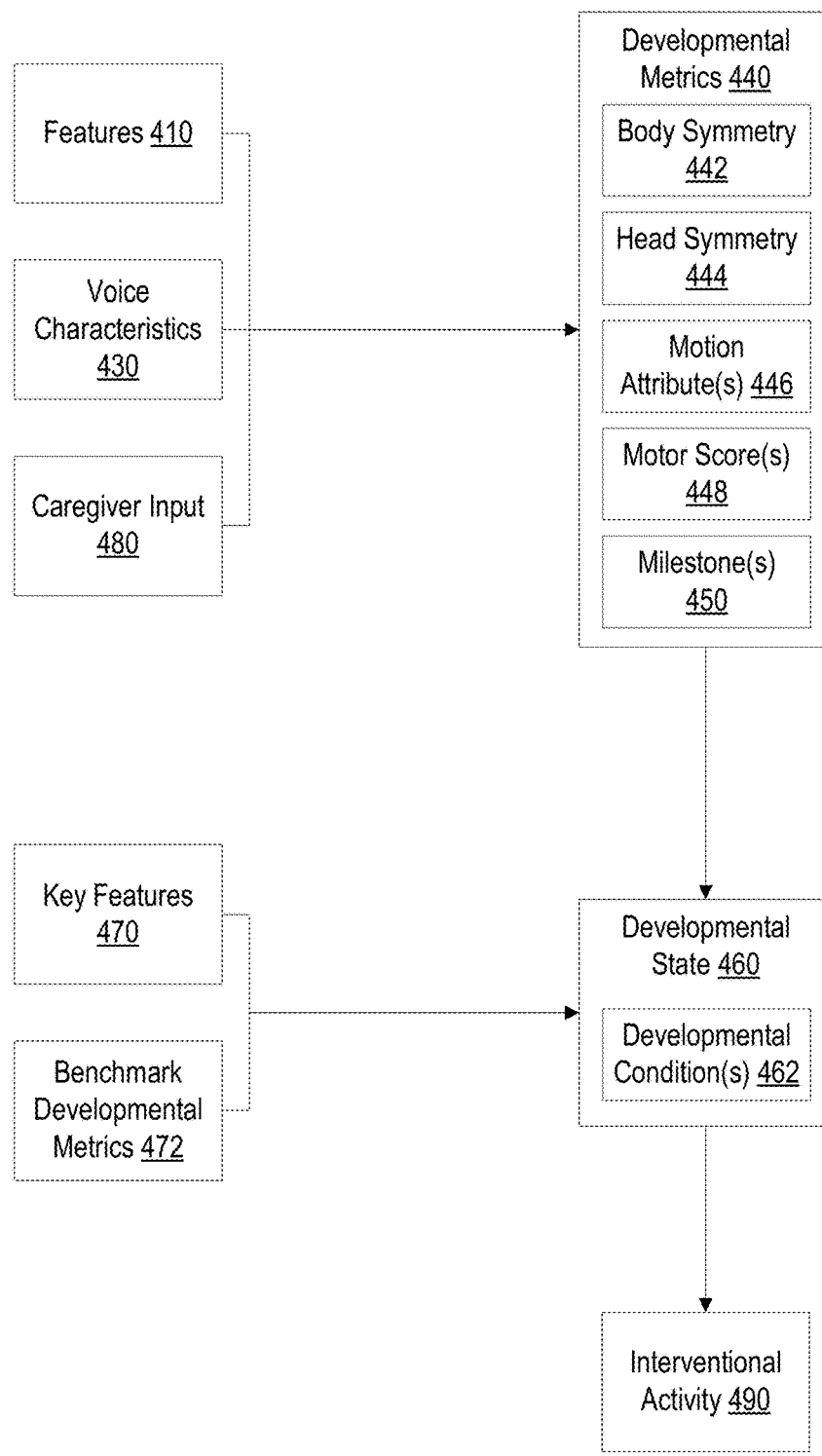
FIG. 4 illustrates a conceptual representation of determining developmental metrics and interventional activities based upon data associated with a subject.

As discussed above, developmental metrics associated with a subject may be determined utilizing features and/or voice characteristics extracted from underlying image data and/or audio data. FIG. 4 illustrates that features 410 (corresponding to features 310) and voice characteristics 430 are usable as input for generating developmental metrics 440. The developmental metrics 440 are indicative of aspects of the human development of the subject that may be inferred based upon body joint positions and/or facial landmarks (as represented by the features 410) and/or voice characteristics 430. The inference of the developmental metrics may be accomplished utilizing rules-based engines, decision trees, mathematical models, artificial intelligence, etc.

The developmental metrics 440 may comprise, by way of non-limiting example, body symmetry 442, head symmetry 444, motion attribute(s) 446, motor score(s) 448, milestone(s) 450, and/or others. Body symmetry 442 and/or head symmetry 444 may comprise indications of bilateral body symmetry in positioning and/or bodily activity for the subject's limbs and/or head. Motion attribute(s) 446 may capture amount of motion/activity, character of motion (e.g., indicating a classification of the motion or behavior captured for the subject based upon the joint positions represented in the features 410), abruptness/acceleration of motion/activity, range of motion, etc. The motor score(s) 448 may comprise a clinically acceptable motor score, such as a Bayley-III motor score, Gross Motor Function Measure, and/or others. The milestone(s) 450 may comprise key developmental activities performed and/or accomplished by the subject, such as crawling, sitting unassisted, tummy time, speaking, and/or others. Performance of such milestones may be inferred from poses represented in the features 410. Other types of developmental metrics are within the scope of the present disclosure.

As indicated above, features 410 and/or voice characteristics 430 may be associated with data captured at different timepoints (e.g., during different recording sessions, or at different timepoints within the same recording session). The developmental metrics may thus correspondingly comprise subsets of developmental metrics associated with different timepoints. In some instances, the developmental metrics 440 comprise overall or longitudinal developmental metrics based upon features 410 and/or voice characteristics 430 obtained over time. Overall or longitudinal developmental metrics may assist in assessing developmental changes or improvements in the subject over time.

FIG. 4 furthermore shows that caregiver input 480 may be utilized as input for determining the developmental metrics 440. Caregiver input 480 (provided by an entity that is distinct from the subject) may take on various forms, such as audio input or text input (e.g., provided at a system or device as described with reference to FIG. 1). For instance, a system may prompt a caregiver to provide supplemental information useful in determining developmental metrics, such as whether the caregiver observed the subject reaching for objects, sitting unassisted, crawling, walking, speaking, experiencing a body spasm, etc. (in the absence of data acquisition that would have captured such events). Such information may be used to update, modify, or assist in determining the developmental metrics 440.

In some instances, caregiver input 480 influences the manner of determining developmental metrics 440 based upon the features 410 and/or the voice characteristics. For example, caregiver input 480 may comprise an indication of a state or situation that the subject will be placed in during data acquisition. Such input may indicate, for example, that the subject will be placed in a supine position, a prone position, or an upright position for a data acquisition session or may indicate a particular activity that will be enacted with the subject for a data acquisition session (e.g., sleep, tummy time, object reaching, name responsiveness testing, etc.). Such context may influence the manner of calculating the developmental metrics 440 and/or which developmental metrics 440 are determined based on the associated features 410 and/or voice characteristics 430.

FIG. 4 illustrates that, in some implementations, a developmental state 460 is determined for the subject based upon the developmental metrics 440. The developmental state 460 may comprise one or more developmental conditions(s) 462 indicative of one or more statuses associated with the development growth or progression of the subject. The developmental condition(s) 462 may comprise, by way of non-limiting example, an indication of the subject's completion or progress toward completion of milestone activities (e.g., crawling, rolling over, sitting and reaching, etc.), an indication of whether the child has failed to complete milestone(s) 450 on time, whether the subject's motor scores are appropriate based on the subject's age, weight, etc., whether the subject exhibits asymmetrical body or head poses and/or activity (e.g., while lying in crib, while sleeping, during guided or unguided activities, etc.), and/or whether the subject exhibits abrupt or spontaneous movements.

In some implementations, the developmental condition(s) 462 may comprise indications of social/emotional progress/delays, language/communication progress/delays, cognitive progress/delays, movement/physical developmental progress/delays (e.g., heightened risk for cerebral palsy, autism spectrum disorder, etc.), and/or others.

In some instances, the developmental condition(s) 462 are determined by comparing the developmental metrics 440 to key features 470 and/or benchmark developmental metrics 472. For example, the key features 470 may comprise facial landmarks (or movements thereof), body joint positions (or movements), voice characteristics, and/or other feature sets indicative of particular activity or behavior (e.g., body or face poses or movements, voice characteristics, etc.) that is/are associated with particular developmental condition(s) 462. In this way, the subject may be indicated as experiencing the particular developmental condition(s) 462 when the developmental metrics 440 of the subject sufficiently correspond to the activity or behavior (e.g., "key activity" or "key behavior") indicated by the key features 470.

For example, key features 470 may comprise body joint positions/locations indicating asymmetrical poses (e.g., while lying in crib, while sleeping, during guided or unguided activities), which may be associated with autism (or risk of autism), such that when the body symmetry 442 of the developmental metrics 440 of a subject corresponds to the asymmetrical poses indicated by the key features 470, the subject may be regarded as at risk for autism. The key features 470 may similarly include vocal characteristics associated with autism. Accordingly, disclosed embodiments may enable detection of the developmental condition 462 of autism, which may allow for appropriate care decisions to be made for the subject.

As another example, a key behavior, attribute, or activity indicated by key features 470 may comprise asymmetric or non-bilateral head tilt, which, if present according to the head symmetry 444 of the developmental metrics 440 and/or features 410 for the subject, may indicate that the subject experiences the developmental condition 462 of torticollis, which, if detected according to the present disclosure, may allow for appropriate care decisions to be made for the subject.

As yet another example, a key behavior, attribute, or activity indicated by the key features 470 may comprise abrupt or spontaneous limb or joint movement, which, if present according to the motion attribute(s) 446 of the developmental metrics 440 and/or features 410 for the subject, may indicate that the subject experiences the developmental condition(s) 462 of cerebral palsy and/or petit/infantile spasms, which, if detected according to the present disclosure, may allow for appropriate care decisions to be made for the subject.

The benchmark developmental metrics 472 may comprise activities and/or behaviors (e.g., milestones) clinically expected to be performable or performed by subjects at particular ages (and/or weights, heights, and/or other aspects). Example benchmark developmental metrics 472 may include social/emotional milestones such as whether the subject, at about 2 months old: is able to calm down when spoken to or picked up, look at faces, exhibit a happy countenance when approached or smiled at or spoken to; at about 4 months old: attempts to get or maintain attention of others, chuckles responsive to attempts to elicit laughter; at about 6 months old: appears to know familiar people, appears to like to look at self in a mirror, laughs; at about 9 months old: appears shy, clingy, or fearful around strangers, shows several facial expressions (e.g., happy, sad, angry, surprised), looks when name is called, reacts when left by caregivers, smiles or laughs responsive to peek-a-boo; at about 12 months old: engages in basic games; at about 15 months old: copies other children while playing, shows others liked by the subject, claps when excited, hugs soft toys, shows affection; etc.

Example benchmark developmental metrics 472 may include language/communication milestones such as whether the subject, at about 2 months old: makes sounds other than crying, reacts to loud sounds; at about 4 months old: responds to talking with sounds, turns head toward the sounds of human voices; at about 6 months old: makes sounds like "ooo", "aahh", or cooing, takes turns making sounds with others, sticks tongue out and blows, makes squealing noises; at about 9 months old: makes a lot of different sounds, lifts up arms to be picked up; at about 12 months old: waves goodbye, calls parents by special names, understands "no"; at about 15 months old: tries to say words in addition to special names for caregivers, looks at objects when named by others, follows directions given with a gesture and words, points to ask for something or to get help; etc.

Example benchmark developmental metrics 472 may include cognitive milestones such as whether the subject, at about 2 months old: tracks moving objects, focuses on objects for several seconds; at about 4 months old: opens its mouth if hungry and in response to seeing breast or bottle, looks at hands with interest; at about 6 months old: puts things in mouth to explore, reaches for desired objects, closes lips to indicate no longer wanting food; at about 9 months old: looks for objects when dropped out of sight, bangs objects together; at about 12 months old: puts objects into containers, looks for things observed as hidden by a caregiver; at about 15 months old: tries to use objects the right way, stacks at least two small objects; etc.

Example benchmark developmental metrics 472 may include movement/physical milestones such as whether the subjects, at about 2 months old: holds up its head when on its tummy, moves both arms and both legs, opens hands briefly; at about 4 months old: holds head steady without support when being held, holds objects when placed in hand, swings objects, brings hands to mouth, pushes up onto elbows/forearms when on tummy; at about 6 months old: rolls from tummy to back, pushes up with straight arms when on tummy, leans on hands to support self when sitting; at about 9 months old: gets to sitting position self-sufficiently, moves things from one hand to the other, uses fingers to rake food towards self, sits without support; at about 12 months old: pulls up to stand, walks holding onto furniture/environment, drinks from cups held by others, picks things up between thumb and finger; at about 15 months old: takes a few steps, uses fingers to feed self some food; etc.

The milestone(s) 450 represented in the developmental metrics 440 may be compared to the benchmark developmental metrics 472 based upon the age (or other aspect) of the subject to determine whether the subject experiences developmental condition(s) 462 such as social/emotional delays, language/communication delays, cognitive delays, movement/physical developmental delays, etc. Detecting such delays according to the present disclosure may allow for appropriate care decisions to be made for the subject. For example, movement/physical developmental delays may be associated with spinal muscular atrophy, the early detection of which may allow for improved subject outcomes.

The benchmark developmental metrics 472 may additionally or alternatively comprise subject attributes that are expected for subjects at particular ages, such as size, weight, motor score, head/body symmetry, range of motion, and/or others. Comparison of corresponding developmental metrics 440 to such benchmark developmental metrics 472 may signal to caregivers that the subject experiences developmental condition(s) 462 such as being underweight or undersized for its age, allowing for intervention to improve outcomes for the subject.

As shown in FIG. 4, an interventional activity 490 (or any number of interventional activities) may be determined (e.g., automatically) based upon the developmental state 460 (and/or information upon which the developmental state 460 is based, such as the developmental metrics 440). The interventional activity 490 may be selected to cause developmental progression relative to the developmental state 460. For example, particular caregiver-subject exercises may be recommended if a subject is determined to be at risk of or experiencing autism, torticollis, cerebral palsy, petit/infantile spasms, and/or other developmental delays, and such interventional activities 490 may be tailored to improve subject outcomes in view of the developmental condition(s) 462 determined to exist for the subject. In some instances, an interventional activity 490 is not tailored to a particular developmental delay associated with the subject, but is rather directed to promoting the subject's progress toward completing developmental milestones on time.

Figure 5:
FIGS. 5 through 8 illustrate example content that may be presented to a caregiver associated with a subject.
Figure 5:
Figure 5:
Figure 5:
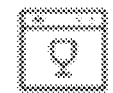
Figure 5:
Figure 5:
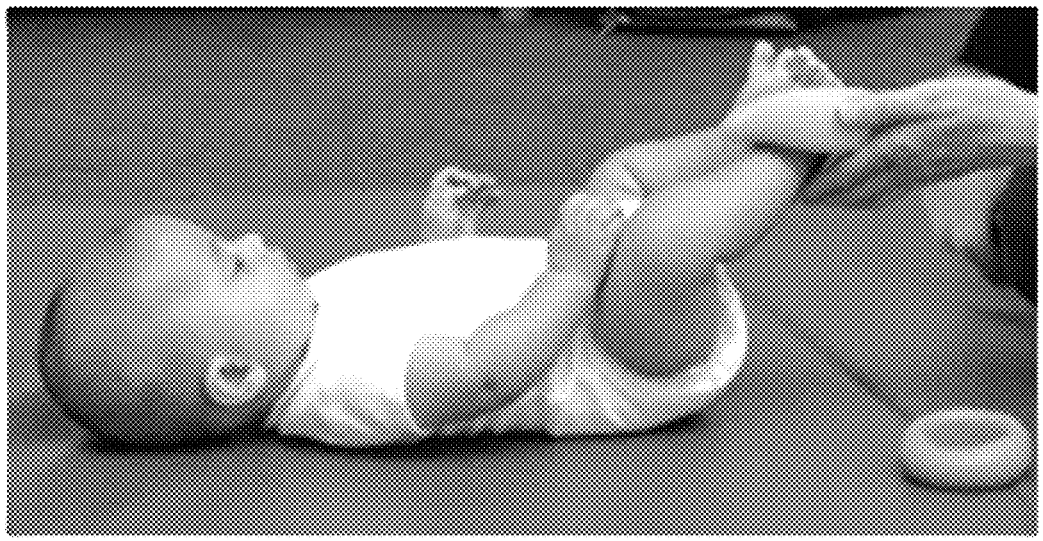
Figure 5:
Figure 5:
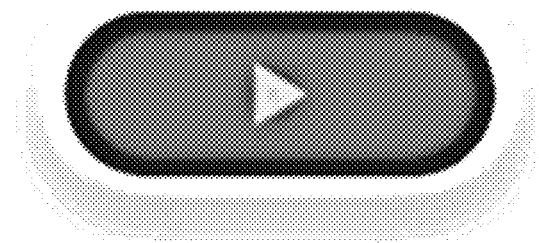

Depictions of the interventional activity 490 may be presented on caregiver devices (e.g., monitoring system(s) 122, smartphone(s) 124, tablet(s) 126, other system(s) 134) to allow the caregiver to facilitate performance of the interventional activity 490 with the subject. For example, FIG. 5 shows a non-limiting, illustrative example of content that may be presented to a caregiver prompting the caregiver to encourage a subject to bring its hands to its feet (indicated by the text "Encourage bringing hands to feet" in FIG. 5). The interventional activity 490 may be queued for performance at particular days/times as appropriate (indicated by the text "Today" in FIG. 5). In some instances, caregivers are presented with information for assisting the caregiver in facilitating the interventional activity 490, such as video instruction, audio instruction, audio-visual instruction, instruction in document or workflow form, etc. Action prompts may include any content necessary to assist the caregiver in facilitating the interventional activity 490, such as how to position the subject, where to position sensors to capture performance of the interventional activity 490 with the subject, what actions to take relative to the subject (e.g., to rattle a toy on one side of the subject, to allow the subject to reach for a toy, etc.), general instructions to keep in mind when caring for the subject (e.g., encourage tummy time, promote bilateral symmetry, encourage reaching for objects, etc.).

In some instances, interventional activities 490 may at least partially be facilitated utilizing I/O system(s) 118 of a system. For example, a system that includes speakers may emit sounds associated with an interventional activity (e.g., playing audio of the subject's name), or a system that includes illuminators may emit light associated with an interventional activity.

Figure 6:
Figure 6:
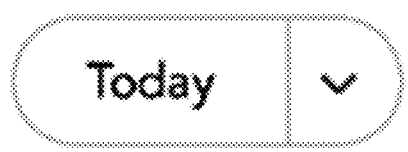
Figure 6:
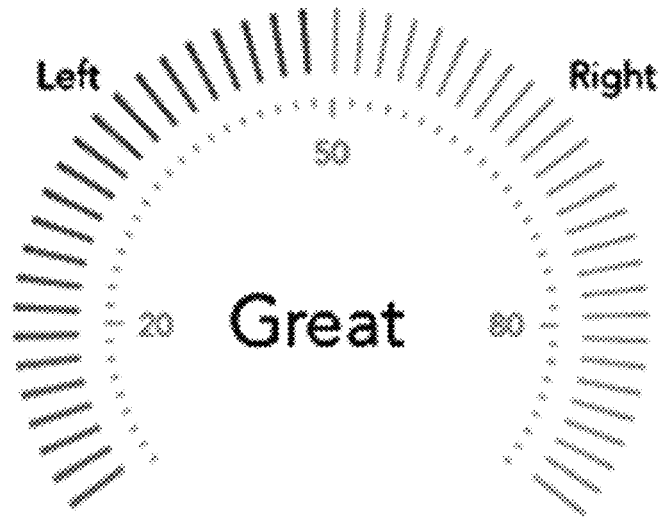
Figure 6:
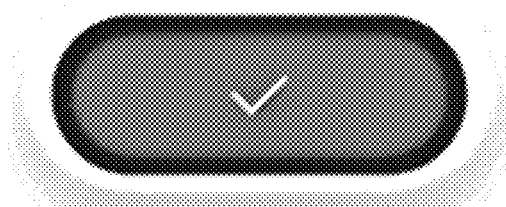
Figure 7:
Figure 7:
Figure 7:
Figure 7:
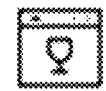

In some implementations, systems are configured to present one or more aspects of the developmental metrics 440 and/or the developmental state 460 on user devices. For example, a report based upon the developmental metrics 440 may be generated and sent to a caretaker of the subject. FIG. 6 provides a non-limiting example of content of a report indicating body symmetry 442 of a subject (named "Ella"). The report of FIG. 6 indicates that body joint positions captured for the subject indicate that the subject exhibits an appropriate amount of body symmetry (indicated in FIG. 6 by the text "Both Ella's left & right sides are engaged"). FIG. 7 provides an additional non-limiting example of content of a report indicating milestone(s) 450 of a subject (named "Ani"). The report of FIG. 7 indicates that the subject has successfully completed various motor milestones, such as "Pull to stand", "Cruising", "Supported Standing", etc. In the example of FIG. 7, the content indicates a date of completion of the milestones (e.g., "May 19" for "Pull to stand", "May 1" for "Cruising", etc.), a number of times the milestone has been captured ("3 events" for "Pull to stand", "several events" for "Cruising", "1 event" for "Supported Standing), and/or an opportunity to play video data (and/or audio data) capturing performance of these milestones by the subject (e.g., via the "Play Video" buttons).

Figure 8:
Figure 8:
Figure 8:
Figure 8:
Figure 8:
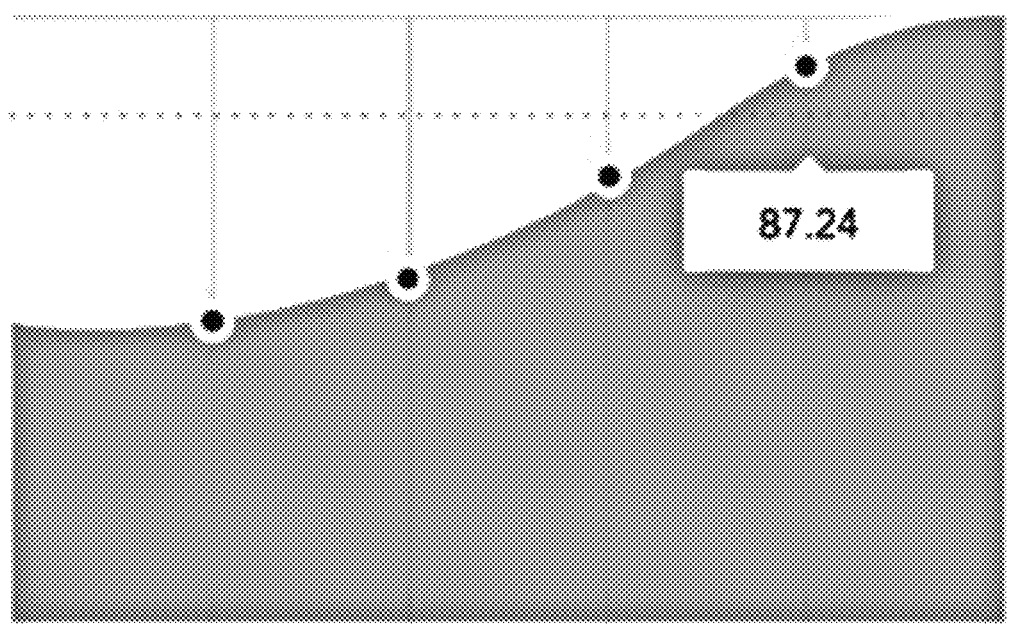

As yet another example, FIG. 8 illustrates example content of a report indicating motor score(s) 448 for a subject (named "Amy"). The report of FIG. 8 indicates longitudinal motor scores for the subject over various weeks, thereby readily conveying the motor developmental trends of the subject. A report generated for a caregiver may additionally or alternatively comprise developmental state(s) 460 of a subject (e.g., indicating developmental conditions, indicating areas of development in which the subject excels or needs improvement, etc.). A report may include information based upon key features 470 and/or benchmark developmental metrics 472 to inform the caregiver of the developmental levels expected for the subject.

Accordingly, image data and/or audio data may be captured of a subject (e.g., a child) in various scenarios, even in the absence of skilled clinicians. The image data and/or audio data may be used to determine developmental metrics for the subject (e.g., based on features extracted from the image data and/or the audio data), which can be used to determine a developmental state for the subject. The developmental state may be used to inform care decisions for the subject's betterment, such as by determining interventional activities that may be enacted to improve the developmental trajectory and/or outcomes of the subject.

The various acts described herein may be performed via execution of instructions at any number of computing entities. For example, in some instances, an end user entity (e.g., a caretaker device, such as monitoring system(s) 122, smartphone(s) 124, tablet(s) 126, sensor(s) 110, and/or other system(s) 134) may perform data acquisition tasks such as operating image sensor(s) 112 and/or microphone(s) 114 to capture image data and/or audio data. The end user entity/ entities may additionally perform at least some additional processing on the captured image data and/or audio data. For example, the end user entity/entities may perform feature extraction processes to determine features as discussed above (e.g., with reference to features 310 and/or voice characteristics 330). The extracted features may then be used by any system to determine the developmental metrics, developmental state, etc. For example, the end user entity/ entities may send the extracted features to a server entity (e.g., server(s) 132) to enable the server to determine developmental metrics and/or developmental states based upon the extracted features, such that the server entity refrains from receiving the image data and/or audio data and only receives the extracted features. When feature extraction is performed at device that captures image/audio, transmission of sizeable image data and/or audio data (e.g., video files) over a network may advantageously be avoided, and video data capturing the subject and/or caretaker may remain private.

Although the present disclosure has focused, in at least some respects, on monitoring development of children, it will be appreciated, in view of the present disclosure, that the principles discussed herein may be applied in other contexts. For example, features extracted from image data and/or audio data passively captured of a subject may be processed to determine whether the subject is experiencing a disease, and interventional activity for addressing the disease may be determined and/or presented to caregivers.

Example Method(s) for Developmental Monitoring of Infants and Toddlers

The following discussion now refers to a number of methods (e.g., computer-implementable or system-implementable methods) and/or method acts that may be performed in accordance with the present disclosure. Although the method acts are discussed in a certain order and illustrated in a flow chart as occurring in a particular order, no particular ordering is required unless specifically stated, or required because an act is dependent on another act being completed prior to the act being performed. One will appreciate that certain embodiments of the present disclosure may omit one or more of the acts described herein.

Figure 9:
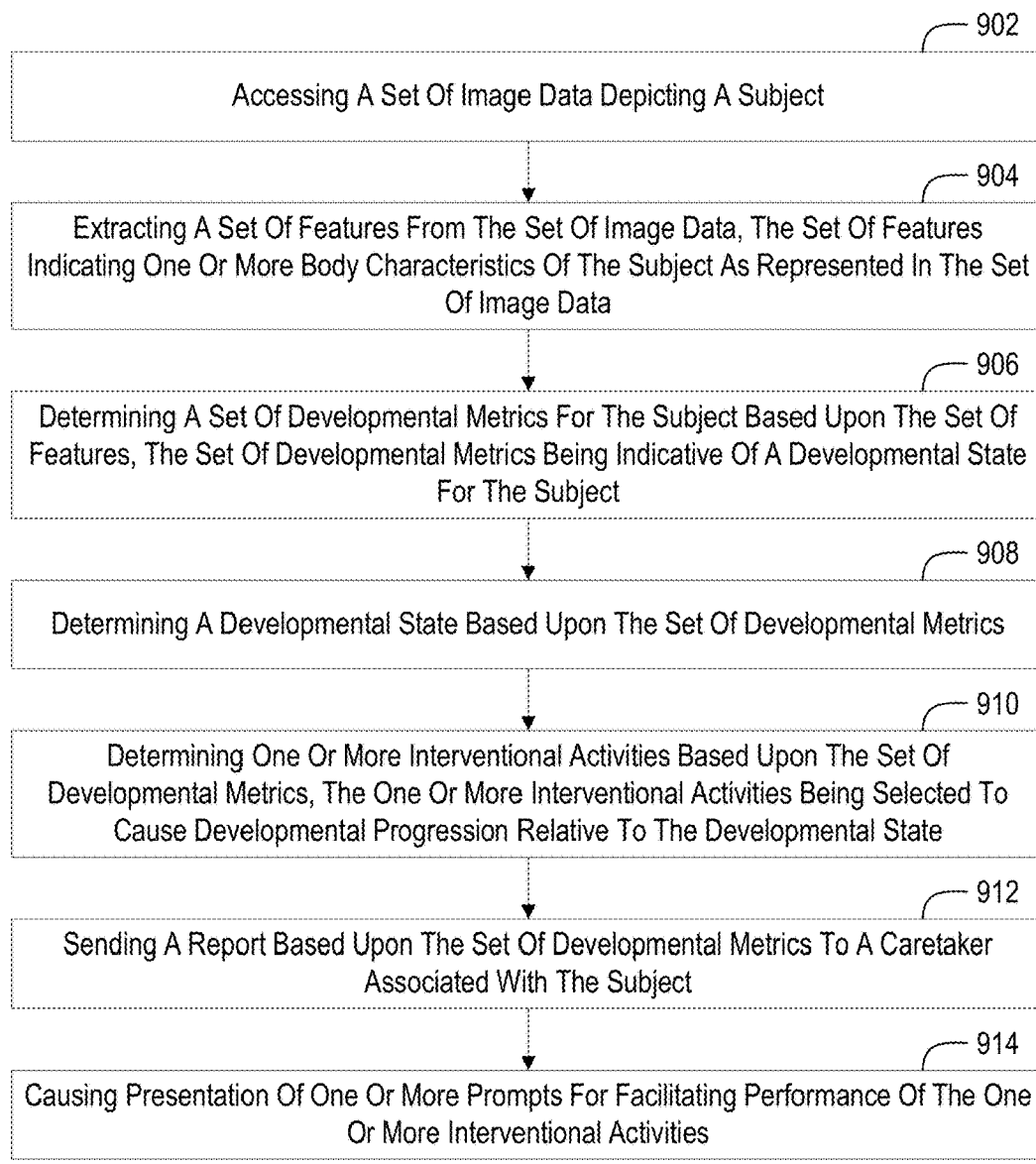
FIG. 9 illustrates an example flow diagram depicting acts associated with developmental monitoring of children.

FIG. 9 illustrates a flow diagram 900 depicting acts associated with developmental monitoring of children. Act 902 of FIG. 9 includes accessing a set of image data depicting a subject. In some instances, act 902 is performed utilizing processor(s) 102, storage 104, sensor(s) 110, I/O system(s) 118, communication system(s) 120, and/or other components. In some instances, the set of image data depicts the subject while the subject engages in one or more unguided activities. In some instances, the set of image data depicts the subject while the subject responds to stimuli or states facilitated by a human guide (e.g., a caretaker). In some implementations, the set of image data comprises a plurality of subsets of image data. Each of the plurality of subsets of image data may associated with different timepoints.

Act 904 of flow diagram 900 includes extracting a set of features from the set of image data, the set of features indicating one or more body characteristics of the subject as represented in the set of image data. In some instances, act 904 is performed utilizing processor(s) 102, storage 104, sensor(s) 110, I/O system(s) 118, communication system(s) 120, and/or other components. In some implementations, the set of features comprises a plurality of corresponding subsets of features (e.g., corresponding to different subsets of image data of a set of image data). Each of the plurality of corresponding subsets of features may be associated with the different timepoints. In some implementations, the set of features is indicative of one or more body joint positions of the subject and/or one or more facial landmarks of the subject.

Act 906 of flow diagram 900 includes determining a set of developmental metrics for the subject based upon the set of features, the set of developmental metrics being indicative of a developmental state for the subject. In some instances, act 906 is performed utilizing processor(s) 102, storage 104, sensor(s) 110, I/O system(s) 118, communication system(s) 120, and/or other components. In some implementations, the set of developmental metrics is determined based on multiple subsets of features of the plurality of corresponding subsets of features (referred to above with reference to act 904). In some instances, the set of developmental metrics is further based upon user input from a user that is distinct from the subject (e.g., a caretaker). In some implementations, the set of developmental metrics is further based upon recorded vocalization of the subject.

Act 908 of flow diagram 900 includes determining a developmental state based upon the set of developmental metrics. In some instances, act 908 is performed utilizing processor(s) 102, storage 104, sensor(s) 110, I/O system(s) 118, communication system(s) 120, and/or other components. In some instances, at least part of the developmental state is based upon a comparison between the set of developmental metrics and a set of benchmark developmental metrics. In some implementations, at least part of the developmental state is based upon detection of one or more key features within the set of features that are associated with one or more developmental conditions. The one or more key features may comprise body joint locations indicating one or more asymmetrical poses for the subject. The one or more key features may comprise body joint locations indicating one or more spontaneous movements of the subject. In some instances, the developmental state is further based upon user input from a user that is distinct from the subject, such as a caretaker. For example, the caretaker may provide conversational input through a device, such as a smartphone, tablet, smart speaker, etc., and developmental states may be at least partially influenced by this conversational input. The conversational input may be responsive to queries provided by a system to supplement the image data (and/or audio data) that has been acquired. By way of illustrative, non-limiting example, a query may comprise, "Have you seen Johnny roll over?".

Act 910 of flow diagram 900 includes determining one or more interventional activities based upon the set of developmental metrics, the one or more interventional activities being selected to cause developmental progression relative to the developmental state. In some instances, act 910 is performed utilizing processor(s) 102, storage 104, sensor(s) 110, I/O system(s) 118, communication system(s) 120, and/or other components.

Act 912 of flow diagram 900 includes sending a report based upon the set of developmental metrics to a caretaker associated with the subject. In some instances, act 912 is performed utilizing processor(s) 102, storage 104, sensor(s) 110, I/O system(s) 118, communication system(s) 120, and/or other components. In some instances, a report comprises developmental insights determined based upon the developmental metrics and/or a developmental state determined for a subject. The report may be sent to parents, clinicians, and/or other caretakers associated with the subject. A report may include various developmental insights, such as time spent on belly, asymmetry of head, asymmetry of limbs, quality of spontaneous movement, motor scores (e.g., over time) etc. (see FIGS. 6 and 8). In some instances, a report enables recipients to view captured data associated with milestones determined to have been performed/achieved by the subject. For example, achievement of milestones (e.g., milestone(s) 450 of FIG. 4) may be determined based upon features extracted from image data (e.g., features 310 extracted from image data 306 of FIG. 3) and/or audio data (e.g., audio data 320 of FIG. 3), and the image data and/or audio data depicting achievement of the milestone may become associated with the report. For instance, a report may include functionality to enable caregivers (e.g., parents) to play video/audio depicting achievement of milestones for the subject. A report (or multiple reports) may thus form a digital memory book for the subject.

Act 914 of flow diagram 900 includes causing presentation of one or more prompts for facilitating performance of the one or more interventional activities. In some instances, act 914 is performed utilizing processor(s) 102, storage 104, sensor(s) 110, I/O system(s) 118, communication system(s) 120, and/or other components.

Additional Details Related to Computing Systems

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are one or more "physical computer storage media" or "hardware storage device(s)." Computer-readable media that merely carry computer-executable instructions without storing the computer-executable instructions are "transmission media." Thus, by way of example and not limitation, the current embodiments can comprise at least two distinctly different kinds of computer-readable media: computer storage media and transmission media.

Computer storage media (aka "hardware storage device") are computer-readable hardware storage devices, such as RAM, ROM, EEPROM, CD-ROM, solid state drives ("SSD") that are based on RAM, Flash memory, phase-change memory ("PCM"), or other types of memory, or other optical disk storage, magnetic disk storage or other magnetic storage devices, or any other medium that can be used to store desired program code means in hardware in the form of computer-executable instructions, data, or data structures and that can be accessed by a general-purpose or special-purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry program code in the form of computer-executable instructions or data structures and which can be accessed by a general purpose or special purpose computer. Combinations of the above are also included within the scope of computer-readable media.

Further, upon reaching various computer system components, program code in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Disclosed embodiments may comprise or utilize cloud computing. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, wearable devices, and the like. The invention may also be practiced in distributed system environments where multiple computer systems (e.g., local and remote systems), which are linked through a network (either by hardwired data links, wireless data links, or by a combination of hardwired and wireless data links), perform tasks. In a distributed system environment, program modules may be located in local and/or remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Application-specific Standard Products (ASSPs), System-on-a-chip systems (SOCs), Complex Programmable Logic Devices (CPLDs), central processing units (CPUs), graphics processing units (GPUs), and/or others.

As used herein, the terms "executable module," "executable component," "component," "module," or "engine" can refer to hardware processing units or to software objects, routines, or methods that may be executed on one or more computer systems. The different components, modules, engines, and services described herein may be implemented as objects or processors that execute on one or more computer systems (e.g., as separate threads).

One will also appreciate how any feature or operation disclosed herein may be combined with any one or combination of the other features and operations disclosed herein. Additionally, the content or feature in any one of the Figures may be combined or used in connection with any content or feature used in any of the other Figures. In this regard, the content disclosed in any one figure is not mutually exclusive and instead may be combinable with the content from any of the other Figures.

CONCLUSION

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatuses disclosed herein may be made without departing from the scope of the disclosure or of the invention. Thus, while various aspects and embodiments have been disclosed herein, other aspects and embodiments are contemplated. All changes that come within the meaning and range of equivalency of the claims are to be embraced within their scope.

What is claimed is:

1. A system for facilitating developmental monitoring of children, comprising:
    one or more processors; and
    one or more hardware storage devices storing instructions that are executable by the one or more processors to configure the system to:
        capture a set of image data depicting a subject, wherein the set of image data comprises a plurality of subsets of image data, each of the plurality of subsets of image data being associated with different image acquisition sessions;
        process the plurality of subsets of image data associated with the different image acquisition sessions using one or more first artificial intelligence modules to extract a set of features from the set of image data, the set of features indicating one or more body characteristics of the subject as represented in the set of image data, wherein the set of features comprises a plurality of subsets of features associated with the plurality of subsets of image data and the different image acquisition sessions; and
        process the plurality of subsets of features associated with the plurality of subsets of image data and the different image acquisition sessions using one or more second artificial intelligence modules to determine a set of longitudinal developmental metrics for the subject based upon the plurality of subsets of features associated with the plurality of subsets of image data associated with the different image acquisition sessions, the set of longitudinal developmental metrics being indicative of a developmental state for the subject.

2. The system of claim 1, wherein the set of features is indicative of one or more body joint positions of the subject and/or one or more facial landmarks of the subject.

3. The system of claim 1, wherein the set of longitudinal developmental metrics is further based upon user input from a user that is distinct from the subject.

4. The system of claim 1, wherein the set of longitudinal developmental metrics is further based upon recorded vocalization of the subject.

5. The system of claim 1, wherein the instructions are executable by the one or more processors to further configure the system to process at least part of the set of longitudinal developmental metrics output via the one or more second artificial intelligence modules to determine the developmental state for the subject.

6. The system of claim 5, wherein at least part of the developmental state is based upon a comparison between the set of longitudinal developmental metrics and a set of benchmark developmental metrics.

7. The system of claim 5, wherein at least part of the developmental state is based upon detection of one or more key features within the set of features that are associated with one or more developmental conditions.

8. The system of claim 7, wherein the one or more key features comprise body joint locations indicating quality of poses for the subject.

9. The system of claim 7, wherein the one or more key features comprise body joint locations indicating one or more spontaneous movements of the subject.

10. The system of claim 5, wherein the instructions are executable by the one or more processors to further configure the system to determine one or more interventional activities based upon the set of longitudinal developmental metrics, the one or more interventional activities being selected to cause developmental progression relative to the developmental state.

11. The system of claim 10, wherein the instructions are executable by the one or more processors to further configure the system to cause presentation of one or more prompts for facilitating performance of the one or more interventional activities.

12. The system of claim 1, wherein the instructions are executable by the one or more processors to further configure the system to send a report based upon the set of longitudinal developmental metrics to a caretaker associated with the subject.

13. The system of claim 1, wherein the system comprises multiple entities including one or more end user entities and one or more server entities, wherein the instructions comprise a first set of instructions executable to cause the one or more end user entities to extract the set of features from the set of image data, and wherein the instructions comprise a second set of instructions executable to cause the one or more server entities to determine the set of longitudinal developmental metrics based upon the set of features extracted by the one or more end user entities.

14. A method for facilitating developmental monitoring of children, comprising:
presenting one or more prompts on an output system of a user device, the one or more prompts directing one or more users to facilitate one or more diagnostic or interventional activities for a subject that is distinct from the one or more users;
capturing a set of image data depicting the subject during performance of the one or more diagnostic or interventional activities;
processing the set of image data using one or more first artificial intelligence modules to extracting a set of features from the set of image data, the set of features indicating one or more body characteristics of the subject as represented in the set of image data during performance of the one or more diagnostic or interventional activities; and
processing the set of features output via the one or more first artificial intelligence modules using one or more second artificial intelligence modules to determine a set of developmental metrics for the subject based upon the set of features, the set of developmental metrics being indicative of a developmental state for the subject.

15. One or more hardware storage devices storing instructions that are executable by one or more processors of a system to configure the system to:
capture a set of image data depicting a subject;
process the set of image data using one or more first artificial intelligence modules to extract a set of features from the set of image data, the set of features indicating one or more body characteristics of the subject as represented in the set of image data;
process the set of features output via the one or more first artificial intelligence modules using one or more second artificial intelligence modules to determine a set of developmental metrics for the subject based upon the set of features, the set of developmental metrics being indicative of a developmental state for the subject;
process at least part of the set of developmental metrics output via the one or more second artificial intelligence modules to determine the developmental state for the subject; and
generate a report comprising (i) the developmental state determined by processing at least the part of the set of developmental metrics output via the one or more second artificial intelligence modules and (ii) a representation of at least the part of the set of developmental metrics output via the one or more second artificial intelligence modules used to determine the developmental state.

16. The one or more hardware storage devices of claim 15, wherein the instructions are executable by the one or more processors to configure the system to:
capture the set of image data depicting the subject using one or more image sensors of a user device, wherein the one or more first artificial intelligence modules are utilized by the user device to process the set of image data to extract the set of features; and
transmit the set of features from the user device to one or more servers while refraining from transmitting the set of image data from the user device to the one or more servers, wherein the one or more second artificial intelligence modules are utilized by the one or more servers to process the set of features to determine the set of developmental metrics, and wherein the developmental state is determined via the one or more servers.

17. The system of claim 5, wherein the developmental state comprises an indication of developmental growth of the subject.

18. The system of claim 5, wherein the instructions are executable by the one or more processors to configure the system to generate a report comprising (i) the developmental state determined by processing at least the part of the set of longitudinal developmental metrics output via the one or more second artificial intelligence modules and (ii) a representation of at least the part of the set of longitudinal developmental metrics output via the one or more second artificial intelligence modules used to determine the developmental state.

19. The system of claim 6, wherein the set of benchmark developmental metrics is determined based on other sets of features extracted from other sets of image data capturing other subjects.

20. The method of claim 14, further comprising:
processing at least part of the set of developmental metrics output via the one or more second artificial intelligence modules to determine the developmental state for the subject; and
generating a report comprising (i) the developmental state determined by processing at least the part of the set of developmental metrics output via the one or more second artificial intelligence modules and (ii) a representation of at least the part of the set of developmental metrics output via the one or more second artificial intelligence modules used to determine the developmental state.

* * * * *